United States Patent [19]

Pearce

[11] Patent Number: 4,532,124

[45] Date of Patent: Jul. 30, 1985

[54] DENTAL RINSE

[75] Inventor: Euan I. F. Pearce, Wellington, New Zealand

[73] Assignee: Development Finance Corporation of New Zealand, Wellington, New Zealand

[21] Appl. No.: 408,410

[22] Filed: Aug. 16, 1982

[30] Foreign Application Priority Data

Aug. 19, 1981 [NZ] New Zealand ............... 198099

[51] Int. Cl.$^3$ .................. A61K 7/16; A61K 7/18; A61K 7/22
[52] U.S. Cl. .................. 424/52; 424/42; 424/54; 424/57
[58] Field of Search .................. 424/49–58

[56] References Cited

U.S. PATENT DOCUMENTS

| | | | |
|---|---|---|---|
| 2,069,157 | 1/1937 | Sahyun | 424/57 |
| 2,542,518 | 2/1951 | Henschel | 424/54 |
| 2,542,886 | 2/1951 | Wach | 424/54 |
| 2,588,992 | 3/1952 | Schlaeger | 424/54 |
| 2,601,238 | 6/1952 | Bell | 424/54 |
| 3,929,988 | 12/1975 | Barth | 424/54 |
| 3,943,241 | 3/1976 | Anderson et al. | 424/54 |
| 3,957,967 | 5/1976 | L'Orange | 424/54 |
| 4,048,300 | 9/1977 | Tomlinson et al. | 424/52 |
| 4,078,053 | 3/1978 | De Paola | 424/52 |
| 4,080,440 | 3/1978 | DiGiulio et al. | 424/52 |
| 4,083,955 | 4/1978 | Grabenstetter et al. | 424/52 |
| 4,108,980 | 8/1978 | Duff, II | 424/52 |
| 4,154,813 | 5/1979 | Kleinberg | 424/54 |
| 4,177,258 | 12/1979 | Gaffar et al. | 424/52 |
| 4,183,915 | 1/1980 | Gaffar et al. | 424/52 |
| 4,198,394 | 4/1980 | Faunce | 424/57 |
| 4,203,966 | 5/1980 | Faunce | 424/57 |
| 4,267,167 | 5/1981 | Weitzman et al. | 424/52 |
| 4,277,464 | 7/1981 | Ruessner et al. | 424/54 |
| 4,348,381 | 9/1982 | Gaffar et al. | 424/52 |
| 4,397,837 | 8/1983 | Raaf et al. | 424/52 |

FOREIGN PATENT DOCUMENTS

| | | | |
|---|---|---|---|
| 149621 | 1/1953 | Australia | 424/54 |
| 2118477 | 10/1971 | Fed. Rep. of Germany | 424/54 |
| 2338177 | 4/1975 | Fed. Rep. of Germany | 424/54 |
| 2404494 | 8/1975 | Fed. Rep. of Germany | 424/54 |
| 2409755 | 9/1975 | Fed. Rep. of Germany | 424/54 |
| 2409756 | 9/1975 | Fed. Rep. of Germany | 424/54 |
| 2409757 | 9/1975 | Fed. Rep. of Germany | 424/54 |
| 2430280 | 1/1976 | Fed. Rep. of Germany | 424/54 |
| 2442712 | 3/1976 | Fed. Rep. of Germany | 424/54 |
| 2647870 | 5/1977 | Fed. Rep. of Germany | 424/52 |
| WO80/02642 | 12/1980 | PCT Int'l Appl. | |
| 1090340 | 11/1967 | United Kingdom | |
| 1222197 | 2/1971 | United Kingdom | 424/52 |
| 1408922 | 10/1975 | United Kingdom | 424/52 |
| 1477823 | 6/1977 | United Kingdom | 424/52 |

OTHER PUBLICATIONS

Robertson et al.; *Clinical Science*, 34:579–594, (1968).
Chughtai et al.; *J. Phys. Chem.*, 72:208–211, (1968).
Smales, *Calcified Tissue Research*, 8:304–319, (1972).
Bell et al.; *Archives of Oral Biology*, 23:329–336, (1978).
Moreno et al.; *Journal of Research of the Nat'; Bureau of Standards—A. Physics and Chemistry*, 72A:773–782, (1968).
Meyer, *Calcified Tissue Int'l*, 27:153–160, (1979).
Nancollas et al.; *J. Phys. Chem.*, 78:2218–2225, (1974).
Moreno et al.; *Soil Science Sco'y of America*, 24:94–98, (1960).
Besic, Chem. Abstracts, 94: 138138y, (1981), of PCT Int. Appl. 80 02642, Dec. 11, 1980.
Caldwell et al., Chem. Abstracts, 74: 11569, (1971).
Mercer et al., Dental Abstracts, 10(7):413–414, Jul. 1965, Caution Needed For Use of Fluoride–Phosphates, Abst. of J. Indiana D.A., 43:424–426, Nov. 1964.
Belting, J. Periodent., 37:20–33, (1966), Effect of Urea on Calculus Formation.
Regolati, C.A. 76: 70651F, (1972) of Helv. Odontol. Acta, Suppl., (1971), 15(7):139–146, "Ammonia and Urea in Oral Pathophysiology".

*Primary Examiner*—Shep K. Rose
*Attorney, Agent, or Firm*—Ladas & Parry

[57] ABSTRACT

The specification describes a dry composition and aqueous solution useful in the mineralization of dental plaque. The solution contains 0.01 to 50% W/V of a substance metabolized by bacteria in plaque (urea is exemplified) to raise the pH of said solution, a physiologically acceptable source of calcium ions and a physiologically acceptable source of phosphate ions, both in concentrations to form a stable solution with respect to a calcium phosphate salt, and optionally a fluoride ion generating compound metabolized by bacteria in plaque to release fluoride ions and/or a water soluble fluoride salt, the pH of the solution being from 1 to 9, and the pH and calcium and phosphate ion concentrations being such that the solution remains stable and with respect to the calcium phosphate salt until the substance is metabolized by bacteria in plaque. Results of some dental trials are presented.

6 Claims, No Drawings

DENTAL RINSE

BACKGROUND OF THE INVENTION

1. Field of Invention

This invention relates to artificial mineralization of dental plaque, a composition and an aqueous solution for carrying out such mineralization.

2. Description of the Prior Art

It is known that calcium and phosphate concentrations in dental plaque vary from person to person and from site to site within the mouth. However plaque calcium and phosphate variations appear to be confined within certain limits. Fluoride concentrations within plaque are less closely controlled.

There is good evidence to suggest that these natural variations in plaque minerals are associated with variations in caries susceptibility. Theoretical considerations indicate that high plaque Ca and inorganic phosphate ($P_i$) levels will lower the 'critical pH', the pH which plaque must reach before it becomes unsaturated with respect to biological apatite, and enamel dissolution commences (Dawes et al., Archs Oral Biol. 7: 161-172 (1962)). In addition, higher concentrations of $P_i$ may increase the buffering action of plaque and may inhibit acid production by certain plaque bacteria (Brown et al., Archs Oral Biol. 22: 521-524 (1977)). Increasing concentrations of plaque F may also be expected to have an increasing caries-protective effect because of this ion's inhibition of microbial glycolysis (Jenkins, Archs Oral Biol. 1: 33-41 (1959)). Thus, it is likely that the higher the concentration of Ca, $P_i$ and F in plaque, the greater will be the protection afforded.

Apart from these theoretical aspects, a protective role for plaque mineral ions is supported by a variety of clinical and experimental observations. Dental calculus, which may be regarded as plaque having a very high concentration of mineral, has long been associated with immunity to caries (Gottlieb: *Dental Caries* p.100 (Lea & Febiger, Philadelphia 1947)).

In plaque having insufficient mineral to be regarded as calculus, increased levels of calcium and phosphate have also been associated with increased resistance to caries. Ashley and Wilson (*Br. Dent. J.* 142: 85-91 (1977)) have found an inverse relationship between the levels of Ca, $P_i$ and organic phosphate ($P_O$) in plaque and the number of tooth surfaces becoming decayed or filled over the first 2 years of a 3-year longitudinal study.

Likewise, clinical studies show that F in plaque tends to protect the enamel against dental caries. The plaque F concentration of children has been inversely related to their individual caries experience (Agus et al, *Community Dent. Oral Epidemiol.* 4: 210-214 (1976)) and to their number of caries-free teeth (*Dental Plaque*, p.p. 171-178 (Livingstone, Edinburgh, 1970)).

It is an object of this invention to go some way towards achieving higher concentrations of Ca, $P_i$ and F in plaque or at least to provide the public with a useful choice.

SUMMARY OF THE INVENTION

Accordingly in one aspect the invention may be said broadly to consist in a dry mix composition containing the following components expressed in parts by weight:

| COMPONENT | PARTS BY WEIGHT |
| --- | --- |
| Urea or other substance metabolised to alkali | 1-500 |
| Source of calcium ions | 0.1-100 |
| Source of phosphate ions and, optionally, | 0.01-20.0 |
| Source of fluorophosphate ions | 0.01-20 |
| Source of fluoride ions | .001-40.0 |

Preferably the composition comprises the following:

| COMPONENT | PARTS BY WEIGHT |
| --- | --- |
| Urea | 5-100 |
| Calcium salt | 1-25 |
| Phosphate salt | 0.3-2.0 |
| Monofluorophosphate salt | 0.1-4.0 |
| Fluoride salt | .006-1.0 |

More preferably the composition comprises the following:

| COMPONENTS | PARTS BY WEIGHT |
| --- | --- |
| Urea | 60 |
| Calcium chloride | 11.1 |
| Sodium dihydrogen phosphate | 0.60 |
| Sodium monofluorophosphate | 0.68 |
| Sodium fluoride | 0.0117 |

Alternatively the composition also contains up to 5 parts by weight of a salt such as KCl, preferably 3 parts by weight.

Although urea is the favoured compound for the dry mix to be used in a plaque mineralising aqueous solution any physiologically acceptable soluble substance which is metabolised by bacteria to produce alkali in plaque can be employed. Typically amino acids such as peptides having 2-4 amino acids, one of which is an arginine unit may be used. Aspartame is another compound that may be substituted for urea.

The source of calcium ions is typically a calcium salt such as calcium chloride, but other physiologically acceptable salts such as calcium lactate, calcium acetate or calcium borate may be selected.

The source of phosphate ions is typically sodium phosphate but any other soluble phosphate may be selected. In the solution embodiment described below phosphoric acid may be used provided the pH is maintained at a level to keep the solution supersaturated.

The fluorophosphate salt is typically a sodium or potassium mono- or hexa- fluorophosphate.

The source of fluoride ions is typically potassium or sodium fluoride.

When the dry mix is to be put into aqueous solution the pH has to be kept sufficiently low to avoid precipitation of calcium phosphate. This may be achieved by controlling the pH during mixing of the dry mix, or alternatively by making a first solution with the first two components and a second solution with the last three components and subsequently combining the first and second solutions.

In another embodiment the invention may be said broadly to consist in a plaque mineralizing aqueous solution comprising 0.01 to 50% W/V of a physiologically acceptable substance metabolised by bacteria in plaque to raise the pH of said solution, a physiologically acceptable source of calcium ions and a physiologically acceptable source of phosphate ions, both in concentrations to form a stable solution with respect to a calcium phosphate salt, and, optionally, a physiologically acceptable fluoride ion generating compound metabolised by bacteria in plaque to release fluoride ions or other physiologically acceptable source of fluoride ions, the pH of said solution being from 1 to 9, with the proviso that the pH and calcium and phosphate ion concentrations are such that the solution remains stable and with respect to said calcium phosphate salt until said substance is metabolised by bacteria in plaque.

Preferably said substance metabolised by bacteria is urea.

Preferably said urea is present in from 3 to 6% W/V.

More preferably said urea is present in 6% W/V.

preferably said calcium salt is calcium chloride.

Preferably said calcium chloride is present in a concentration of 100 mM.

Preferably said phosphate salt is $NaH_2PO_4$.

Preferably said $NaH_2PO_4$ salt is present in a concentration of 5 mM.

Preferably said fluoride ion generating compound is also a phosphate ion generating compound.

More preferably said fluoride ion generating compound is $Na_2PO_3F$.

Preferably said $Na_2PO_3F$ is present in a concentration such that the total fluoride concentration to be generated within the solution is 5 mM.

Preferably the pH of said solution is from 4 to 5.

More preferably the pH of said solution is 5.

In another alternative an additional salt is present.

Preferably said additional salt is KCl.

Preferably said KCl is present in a concentration of 0.04 M.

In another preferred embodiment the invention may be said broadly to consist in a mouth rinse which comprises an aqueous solution containing:

| | | |
|---|---|---|
| urea | 3% (w/v) | |
| calcium chloride | | 12 mM |
| sodium dihydrogen phosphate | | 12 mM |
| sodium monofluorophosphate | | 4.72 mM |
| sodium fluoride | | 0.28 mM |
| glycerol | 5% (v/v) | |
| saccharine | | to increase palatability |
| spearmint | | |
| vanilla | | |
| food colour | | |
| adjusted to pH 5.0. | | |

The invention consists in the foregoing and also envisages constructions of which the following gives examples.

EXAMPLE 1

Removable intra-oral appliances were constructed for 2 female and 3 male adults (Pearce et al., *N.Z. Dent. J.* 75: 8–14 (1979)), after a design of Koulourides. The appliances carried two 3×4 mm slabs of bovine enamel mounted in the buccal sulcus adjacent to the lower first permanent molar, one on the left side of the mouth and one on the right. Each pair of enamel slabs was cut from the same bovine incisor crown after it had been sterilised in ethylene oxide and the enamel surface ground flat with 600 mesh carborundum and smoothed with 5 $\mu$m alumina. The enamel surface was covered with 2 layers of a fine "Dacron" (a trade mark) gauze to accelerate plaque formation.

The appliances were worn continuously for 2 days to establish a plaque and then, for the next 5 days, periodically removed from the mouth for exposure to the mineralizing solution. Plaque was treated either for 10-min periods 3 times per day, or for 15-min periods 4 times per day, with a minimum of 2 h between treatments. Plaque on only one side was treated, the contralateral side acting as a control. The whole appliance was rinsed in tap water before being replaced in the mouth. The appliances were always worn overnight and during meal-times.

The plaque mineralizing solution contained 6% urea, 0.04 M KCl, 100 mM $CaCl_2$, 5 mM $NaH_2PO_4$, 4.72 mM sodium monofluorophosphate (MFP), 0.28 mM $F^-$ and was adjusted to pH 5.0. All chemicals were Analar grade except sodium monofluorophosphate which was a commercial sample. The solution was stored at 5°. For use, a 10-ml sample was preheated to 37° C. and the appropriate flange of the appliance dipped into the solution while the temperature was held constant at 37° C.

On the morning following the final treatment day, at least 16 hours after the last plaque treatment, the appliance was removed from the mouth, excess saliva removed by blotting with filter paper, and the 3×4 mm "Dacron" 'plaque gauzes' excised. Remaining plaque was scraped from the enamel surface with a chisel-shaped piece of soft polythene, and both gauzes and scrapings extracted in 0.5 ml of 0.5 N $HClO_4$ for 12 hours in a capped 1-ml polystyrene vial. The acid extract was analysed for $P_i$ by a phosphomolybdate method (Chen et al., *Analyt. Chem.* 28: 1756–1758 (1956)) and for Ca by flame photometry, using 1% lanthanum to overcome phosphate interference. F was estimated with a specific ion electrode (Orion model 96-09) after the neutralization of 100 $\mu$l aliquots with 10 $\mu$l of 5 N NaOH and the addition of TISAB (Orion) containing sufficient F to ensure a minimum final concentration of 0.02 ppm. The plaque residue was heated in 0.5 ml of 1.7–1.9 N NaOH at 80°–90° C. for 45 min and the protein content determined (Lowry et al., *J. Biol. Chem.* 193: 265–275 (1951)) using bovine serum albumin as a standard.

Plaque gauzes from one experiment utilising the longer and more frequent exposure periods were dried in air and subjected to X-ray diffraction analysis (Philips model PW 1050/25 using Ni filtered Cu $K_\alpha$ radiation).

The effects on dental plaque of treatment with the mineralizing solution for 10-min periods, 3 times per day for 5 days are shown in table I. In this series of experiments each subject used the solution for two 5-day periods; once to treat plaque on the left side of the mouth and once to treat plaque on the right. The contralateral side always served as a control. The results are expressed as $\mu$g of Ca, P or F/mg protein since the unknown amount of "Dacron" present in each gauze made dry weights impossible to obtain.

TABLE I

| | | | \multicolumn{6}{c}{Mineralization of dental plaque in 5 subjects} |
|---|---|---|---|---|---|---|---|---|
| | | | \multicolumn{6}{c}{Plaque minerals, μg/mg protein} |
| Subject | Side treated | Plaque position | calcium | | phosphate[1] | | fluoride | |
| | | | treated | control | treated | control | treated | control |
|---|---|---|---|---|---|---|---|---|
| A.P. | left | outer | 187 | 5.32 | 101 | 4.05 | 5.75 | 0.013 |
| A.P. | left | inner | 169 | 13.3 | 88.8 | 5.92 | 4.61 | 0.009 |
| A.P. | right | outer | 396 | 4.21 | 194 | 4.25 | 19.7 | 0.016 |
| A.P. | right | inner | 266 | n.d. | 165 | n.d. | 16.5 | n.d. |
| J.W. | left | outer | 310 | 11.5 | 158 | 4.63 | 7.27 | 0.012 |
| J.W. | left | inner | 307 | 13.7 | 156 | 5.26 | 7.17 | 0.001 |
| J.W. | right | outer | 210 | 6.20 | 109 | 3.80 | 14.4 | 0.009 |
| J.W. | right | inner | 170 | 10.4 | 95.6 | 6.26 | 13.2 | 0.0 |
| E.P. | left | outer | 293 | 6.22 | 160 | 6.04 | 16.1 | 0.005 |
| E.P. | left | inner | 295 | 9.74 | 191 | 11.8 | 17.6 | 0.009 |
| E.P. | right | outer | 306 | 3.82 | 148 | 1.22 | 22.8 | 0.032 |
| E.P. | right | inner | 238 | 7.28 | 118 | 0.0 | 14.0 | 0.0 |
| A.M. | left | outer | 220 | 4.75 | 105 | 4.95 | 10.2 | 0.012 |
| A.M. | left | inner | 166 | 8.83 | 89.9 | 5.50 | 7.28 | 0.062 |
| A.M. | right | outer | 56.8 | 2.11 | 22.7 | 1.52 | 3.84 | 0.013 |
| A.M. | right | inner | 104 | 4.71 | 45.0 | 0.0 | 7.25 | 0.017 |
| A.W. | left | outer | 729 | 7.79 | 368 | 4.01 | 20.2 | 0.008 |
| A.W. | left | inner | 607 | 26.0 | 357 | 9.81 | 16.4 | 0.010 |
| A.W. | right | outer | 445 | 12.1 | 216 | 2.64 | 12.2 | 0.020 |
| A.W. | right | inner | 362 | 16.5 | 180 | 3.52 | 10.2 | 0.032 | n.d. = Not determined because plaque sample was too small (<0.01 mg protein). 'Outer' plaque was the material contained in the dacron mesh, 'inner' plaque was the material scraped from the enamel surface.
[1] μg phosphorus/mg protein.

The concentrations of acid-extractable $Ca$, $P_i$ and $F$ increased markedly in each subject's plaque after treatment with the solution. There were considerable differences in amounts deposited in the 2 experiments in each subject as well as between subjects. However, the 2 highest values for treated plaque $Ca$ and $P_i$ concentrations were found in 1 subject (A.W.), while the subject having the lowest amount deposited (A.M.) also had a low amount deposited when the contralateral plaque was treated. Rather more mineral appeared to be deposited in the outer plaque (represented by the material contained within the "Dacron" gauze) than in the inner plaque (represented by the material which could be scraped from the enamel surface after removal of the gauze), although this variation appeared to be less than the 'between subject' or 'between side' variations. The mean Ca concentration of the 10 treated plaques (outer and inner plaque material combined) was 307±176 μg/mg protein (mean+1 SD) compared with a value of 7.59±3.37 for the untreated plaque. The $P_i$ concentration of treated plaque was 157±90.1 μg/mg protein (untreated Plaque $P_i$ concentration 4.02±1.90) and the F concentration 13.0±6.15 μg/mg protein (untreated plaque F concentration 0.014±0.007).

The average amount of protein in plaque developing on the treated side was 0.45±0.11 mg while a similar amount was found in plaques from the untreated side, 0.41±0.09 mg. The outer plaque samples (in the gauzes) contained an average of 0.33±0.09 mg protein while the inner plaque samples (enamel scrapings) contained an average of only 0.09±0.04 mg.

After subtracting values for Ca and $P_i$ found in plaque on the control side, the mineral deposited in the treated plaques had a Ca:P (molar) ratio of 1.55±0.14. There was a very high correlation between the increase in Ca and the increase in $P_i$ in the plaques ($r = +0.997$), and although the F concentration also tended to increase with the Ca concentration, this correlation was not as strong ($r = +0.621$). The Ca:F ratios varied from 6.5 to 20.3.

X-ray diffraction analysis of an outer plaque gauze sample which had been treated for 15-min periods, 4 times per day, clearly showed the presence of a well-crystallized apatite mineral phase. The main peaks of hydroxyapatite were clearly separated and most of the peaks having a relative intensity > 10 seen. There was no evidence of the presence of octacalcium phosphate, brushite, calcium fluoride or whitlockite, although the most useful peak for identifying this latter compound in the presence of hydroxyapatite (d = 3.21 Å) would have been obscured by the 3 very large and broad peaks resulting from the "Dacron" (d = 3.44, 3.86 and 4.95 Å). Plaque from the untreated control side showed these "Dacron" peaks only.

The 40-fold increases in Ca and $P_i$ and the 900-fold increase in F found in treated plaque more than 16 h after the last treatment are greater than any previously reported in the literature following attempts to mineralise plaque artificially. Any high levels of $P_i$ or F obtained previously have declined again to normal levels within 3 h of treatment (Tatevossian, *Proc 20th ORCA Congr. Helv. Odont. Acta* 17: 51 (1973); Tatevossian et al., *Archs Oral Biol.* 24: 461–466 (1979)). Retaining one plaque as an untreated control while reversing treatment sides showed that the mineralisation was not an effect related to saliva, rather than the treatment (e.g. due to one plaque gauze lying close to the orifice of the parotid duct). However, this does not exclude the possibility that the natual mineralising ability of the saliva increased the plaque mineral content once it had been nucleated by solution treatment.

The high correlation between the increase in Ca and the increase in $P_i$ in treated plaque indicates that these ions were precipitated together as a mineral phase. Although X-ray diffraction revealed the presence of only apatite in the sample analyzed, it is possible in view of the low initial pH that small amounts of brushite were also precipitated (Newesely, *Caries Res.* 2: 19–26 (1968)). This could account for the lower Ca:P ratios of 1.38 and 1.45 which were found in two of the samples. F can cause the conversion of brushite to apatite (Chow, *J. Dent. Res.* 52: 1220–1227 (1973)) but it is not known if the small but variable amount of F present (about 5 ppm) would be sufficient to inhibit brushite forming in the plaque. Alternatively, the low Ca:P ratios may be explained by the formation of a Ca-deficient apatite.

F uptake was less well correlated with Ca uptake but this would not exclude its co-precipitation in an apatite phase. F can be incorporated in a continuously variable amount (from none to the 3.77% in fluorapatite)—its inclusion depending on concentration and pH (Le Geros, IADR 58th General Session, Abstr No. 344, J Dent. Res 59 special issue B p. 973 (1980)). Both of these factors would have differed from run to run in the present series, depending on the MFP-degrading and the ureolytic abilities of the particular plaque. However, the Ca:F ration of 6.5 achieved in one sample indicated that maximum incorporation as fluorapatite was being approached.

EXAMPLE 2

In another experiment an adult subject ceased toothbrushing and other usual oral hygiene practices for 4 days in order to allow natural dental plaque to accumulate. On the final 3 days of this period, the subject mouthrinsed for 2 consecutive 1-minute periods, 4 times per day, with a modified plaque-mineralizing mouth rinse solution. Fifteen ml of fresh solution, preheated to 37° C., was used for each minute and then expectorated. The mouthrinse contained:

| | |
|---|---|
| urea | 3% (w/v) |
| calcium chloride | 20 mM |
| sodium dihydrogen phosphate | 12 mM |
| sodium monofluorophosphate | 4.72 mM |
| sodium fluoride | 0.28 mM |
| glycerol | 5% (v/v) |
| saccharine | sufficent to |
| spearmint | increase |
| vanilla | palatability |
| food colour | |
| adjusted to pH 5.0 | |

At the end of the 4-day experiment period, natual plaque was collected from the buccal surfaces of upper premolar, canine and incisor teeth with a plastic dental instrument, palced in a platinum dish and the dry weight obtained. Plaque was then analysed for acid-extractable calcium, phosphate, fluoride and protein content as described previously. For comparison, untreated control plaque was collected after a similar 4-day period when the rinsing solution was not used. The effect of in vivo use of the modified plaque mineralizing solution is seen in table II. The solution increased the concentration of Ca, $P_i$ and F markedly, to levels comparable to those achieved with the original formulation used in vitro, even though the total plaque exposure time was only 24 min compared to 150 min in the experiments using the appliances. The result of this experiment indicates that the dental plaque which grows natualy on teeth in the mouth can be mineralized by repeated short treatments with the urea and MFP-containing mineralizing solution as readily as plaque which grows on removable appliances.

TABLE II

| In vivo mineralization of natural dental plaque | | | | | |
|---|---|---|---|---|---|
| Plaque minerals μg/mg protein | | | | | |
| Calcium | | phosphate[1] | | fluoride | |
| treated | control | treated | control | treated | control |
| 337 | 12.0 | 185 | 11.1 | 3.34 | 0.071 |

[1]μg phosphorus/mg protein

It is to be understood that the subject ceased usual oral hygiene practices for ease of analytical technique. Plaque was allowed to accumulate to allow a sufficient amount to be collected for straight forward analyses. This not to suggest that there not sufficient plaque remaining after toothbrushing to allow the treatment to have beneficial effects on persons carrying out normal oral hygiene practices.

EXAMPLE 3

Effect of Plaque Mineralisation on Experimental Dental Caries

Removable lower arch appliances were constructed for 5 adult subjects. Extensions into the right and left buccal sulci, adjacent to the 1st permanent molars, held two plaque gauze-enamel units each. A unit consisted of a 3×4 mm piece of bovine enamel covered with two layers of fine terylene gauze and was mounted in a recess in the acrylic buccal extension with an epimine resin. Two enamel pieces were cut from the same permanent bovine incisor crown and these were always used as a matched pair—one being mounted on the left and one on the right side of the appliance. Two such pairs were used in each appliance.

Following sterilisation of the tooth pieces in ethylene oxide, the original surface was removed with 600 mesh carborundum and the underlying enamel polished to a high gloss with alumina and diamond abrasives. Initial hardness testing was then carried out, gauze layers were added, and the dry units stored.

For the first 2 days of the 14-day experimental period the appliance was worn continuously to establish a plaque growth within the terylene gauze. During the next 5 days the appliance was removed from the mouth three times per day and the plaque-enamel units on the right (test) side exposed to a plaque-mineralising solution for 10 min. The plaque-enamel units on the left (control) side were kept in a humid atmosphere during this period. The whole appliance was then rinsed in tap water and replaced in the mouth. After the first 7 days, i.e., halfway through the experiment, one pair of matched plaque-enamel units was removed for analysis (a unit from each side) and the appliance worn continuously for a further 2 days. On the last 5 days of the experiment the appliance was again removed from the mouth for 10-min periods, three times per day, but this time both left and right sides were exposed to a cariogenic solution. Finally, the remaining matched pair of plaque-enamel units was removed for analysis. Appliances were always worn overnight and during meals, but were removed at normal toothbrushing times when the acrylic surfaces were cleaned, a non-fluoride toothpaste being used.

The plaque-mineralising solution contained 6% urea 0.04 M KCl, 100 mM $CaCl_2$, 5 mM $NaH_2PO_4$, 4.72 mM $Na_2PO_3F$, 0.28 mM NaF, and was adjusted to pH 5.0. The cariogenic solution contained 5% glucose and 0.04 M KCl, pH 7. All chemicals were Analar grade except sodium monofluorophosphate which was a commercial sample. Both solutions were stored at 5° C., but were preheated to 37° C. and held at this temperature during use.

The gauzes (outer plaque) were excised from the enamel pieces, the remaining (inner) plaque was scraped from the enamel surface with a chisel-shaped piece of soft polythene, and both gauzes and scrapings extracted in 0.5 ml of 0.5 N $HClO_4$ for 12 h in a capped 1-ml polystyrene vial. The supernatant acid extract was analysed for $P_i$ by a molybdate method [Chen et al., Analyt. Chem. 28: 1756-1758, (1956)] and for calcium by flame photometry, using 1% lanthanum to overcome phosphate interference. Fluoride was estimated with a specific ion electrode (model 96- 09; Orion Research, Cambridge, Mass., U.S.A.) after neutralisation of 100 μl aliquots with 10 μl of 5 N NaOH and the addition of 100 μl of Tisab (Orion). The plaque residue was heated in 0.5 ml of 1.8 N NaOH at 80°-90° C. for 45 min and the protein content determined according to the method of [Lowry et al J. Biol. Chem. 193:265-275 (1951)], using bovine serum albumin as a standard.

Hardness testing of the enamel was carried out with a Knoop diamond and a 50-gram load (Leitz miniload; Leitz, Wetzlar, FRG). Each piece was initially tested with a predetermined pattern of 12 indentations and then retested after an experiment with a further 12 indentations, again following a predetermined pattern. Occasionally during retesting a mineral deposit partly obscured the polished enamel surface and then the indentations were placed wherever possible. The difference in average length of the diamond indentations before and after an experiment served as a measure of enamel softening. The significance of the difference (i.e., of the softening) was tested by the method of [Welch Biometra 34:28-35 (1947)].

Finally, each enamel piece was sectioned with a watercooled diamond saw and the sections ground to 50-60 μm thickness [Sundstrom, Acta Odont. Scand. 24:159-178, (1966)]. Radiography was performed with a Softex CMR X-ray generator (Hosoda, Tokyo, Japan) on Kodak 649-0 spectroscopic film. The X-ray wave length was approximately 2.5 Å and the exposure time 15-25 min.

Results

Changes in Plaque Mineral Ion Concentrations

Treatment of plaque with the urea-MFP mineralising solution from day 3 to day 7 increased its average calcium concentration from 7.6±1.7 μg/mg protein (the value on the control side) to 219±111 μg/mg protein (mean of combined, i.e., outer+inner, plaque material from 5 subjects±1 SD). During this period, when normal dietary conditions were maintained, acid-extrable $P_i$ also rose from 5.4±0.6 to 107±52.7 μg/mg protein and fluoride from 0.008±0.004 to 7.62±1.43 μg/mg protein. The final concentrations were more often higher in outer plaque contained within the terylene gauze than in inner plaque scraped from the enamel surface. Increases in calcium were closely related to increases in $P_i$ and fluoride. The calcium/phosphate molar ratio of the increases for combined plaque material was 1.60±0.08 while the calcium/fluoride molar ratio was 7.29±1.40.

The cariogenic conditions subsequently prevailing from days 10-14 caused marked reductions in all three ions in the treated plaques. Nevertheless, they were, with few exceptions, still higher than in untreated (control) plaques. The average calcium concentration of combined plaque material was now 59.6±39.4 μg/mg protein (compared to 6.5±1.8 in the control), $P_i$ 32.7±20.0 (compared to 7.5± 1.8), and fluoride 4.27±3.49 μg/mg (compared to 0.007±0.004 μg/mg protein). In absolute terms, greater losses were associated with greater amounts deposited initially. The mineral-depleting effect of the glucose exposures was most pronounced in outer plaque material and in 1 subject (A.M.), deposited calcium and $P_i$ was almost completely lost. Similar percentages of calcium and $P_i$ were lost from plaque, but in 3 subjects relatively less fluoride was lost. Overall, in 5 subjects and for combined plaques, the mineral remaining after glucose exposures (control values subtracted) had a calcium/phosphate ratio of 1.68±0.43 and a calcium/fluoride ratio of 6.28±1.20.

Changes in Enamel Hardness and Radiopacity

Enamel beneath untreated plaque (control), exposed to a normal diet for 7 days, always showed a small but variable degree of softening. The increase in Knoop diamond indentation length averaged for the 5 subjects was 3.7 μm. Under mineralised plaque, matched enamel exposed to similar dietary conditions showed much less softening, an average 1.3 μm increase, representing a 65% reduction. In 2 subjects there was no significant change in hardness and in another the softening was of marginal significance. These small decreases in enamel hardness could not be detected by microradiography.

Enamel beneath untreated plaque exposed to a cariogenic challenge during a further 7 days in the mouth showed marked softening. The average increase in indentation length was 25.0 μm. Except in the subject showing the smallest reduction in hardness, the enamel showed distinct subsurface radiolucent areas on microradiography. By contrast, under mineralised plaque, matched enamel exposed to the same cariogenic challenge showed much less softening. The average increase in indentation length was only 4.3 μm, representing an 83% reduction over the control enamel samples. No radiolucent areas were detected in enamel beneath mineralised plaque.

Plaque Minerals and Enamel Softening

There was no apparent association between the concentrations of calcium, $P_i$ and fluoride in plaque and the degree of softening of the underlying enamel on the control side of the appliance. However, a distinct inverse association appeared on the experimental side. During both the initial 7 days of normal dietary conditions and the subsequent period of cariogenic challenges, greater amounts of mineral in plaque were associated with less enamel softening. In the latter period, softening was negligible when a large amount of mineral was retained in plaque. Conversely softening was greatest where outer plaque calcium and $P_i$ had been reduced to near control levels.

EXAMPLE 4: IN VIVO STUDIES

Fifteen student school dental nurses, mean age 18 years 6 months, volunteered to take part in the trial. A control phase in which normal oral hygiene was withheld for 4 days was followed 3 weeks later by 4-day experimental phase when, in addition to withholding oral hygiene, the mouthrinse solution was used. Plaque samples were collected at the end of each phase. The subjects were examined on the morning of the first day of both control and experimental periods and areas of gingivitis and supragingival calculus recorded. The clinical crowns of all teeth were then cleaned of soft deposits using a rubber cup and non-fluoride toothpaste. The subjects were again examined on the morning of the 5th day when all available supragingival plaque was collected from the buccal and lingual surfaces of teeth 15-25, 34-37, and 44-47 (FDI notation), using a soft plastic instrument ("Delrin", DuPont). Remaining plaque was then disclosed with erythrosine and removed with a prophylaxis paste (Nupro fine grit). Finally, the subjects rinsed for 30 secs with a 0.2% chlorhexidine solution ("Savacol", I.C.I.).

During the experimental phase the plaque mineralising mouthrinse was used 4 times per day on days 2, 3 and 4, at 2-hourly or longer intervals. At each rinsing period approximately 15 ml of solution was swished around the mouth for 1 min, spat out and the process repeated once.

The mouthrinse was the same as that of Example 2. The solution was stored at 5° C. but was warmed to 37° C. for use.

Plaque samples were placed in small tared platinum dishes and, after 16 h in a vacuum at 40° C. over $P_2O_5$, dry weights were obtained. The samples were extracted in 0.5 ml of 0.5 N $HClO_4$ overnight and phosphate determined in the supernatant by a molybdate method, calcium by flame photometry using 1% La to overcome phosphate interference, and fluoride by a specific ion electrode (Orion model 94-09). The samples were then heated in 2N NaOH at 80°–90° C. for 45 min and the protein content determined. Bovine serum albumin was used as a standard.

Results

Rinsing with the mineralising solution over 3 days resulted in an 80-fold increase in the average concentration of acid-extractable fluoride in plaque, a 13-fold increase in calcium and a 6-fold increase in phosphate. While plaque of every subject showed some effect, there was a large individual variation in response. Increases in fluoride ranged from 32 to 1535 $\mu g$/mg dry wt, increases in calcium from 1.0 to 97.7 $\mu g$/mg and increases in phosphate from 0.4 to 44.6 $\mu gP$/mg.

Increase in plaque calcium was very strongly related to increase in phosphate ($r = +0.99$, $P < 0.01$) and the Ca/P molar ratios of the increases averaged 1.64. Increase in calcium was less strongly related to increase in fluoride ($r = 0.70$, $P < 0.01$) and the Ca/F molar ratios of the increases averaged 34.2 (range 16.2 to 68.9).

The magnitude of the increases in calcium and phosphate tended to be related to the initial concentrations of these ions (i.e. in the control plaque); $r = +0.71$, $P < 0.01$ in both cases. However there was no corresponding trend with respect to increases in fluoride. A number of subjects had small amounts of supragingival calculus on lingual surfaces of lower anterior teeth at the initial examination but there was no apparent association between this and subsequent increases in calcium, phosphate or fluoride.

The protein concentration in the control plaque was 484±46 $\mu g$/mg (mean±s.d.) and in the experimental plaque 437±40 $\mu g$/mg dry wt. The average dry weight of control plaque collected was 1.78±0.97 mg and experimental plaque, 2.50±1.15 mg.

EXAMPLE 5: NON-FLUORIDATED CALCIUM PHOSPHATE

In the previous examples the mouth rinses described all contained a source of fluoride ions. A satisfactory rinse solution could also be prepared without a source of fluoride ions. Such a mouth rinse would deposit mineralising calcium phosphate salt. This would not provide as much caries protection as would the solution which did have a fluoride source but it would be an improvement over no treatment at all.

What is claimed is:

1. In the art or method of mineralizing dental plaque, the improvement consisting of the step of treating said plaque with a plaque mineralizing aqueous solution comprising 0.01 to 50% W/V of urea, a physiologically acceptable water-soluble fluoride salt, a physiologically acceptable water-soluble calcium salt and a physiologically acceptable water-soluble phosphate salt, the pH of the solution being from 1 to 9; said salts being present in concentrations such that the pH and fluoride, calcium and phosphate ion concentrations are such that the solution remains stable with respect to a calcium phosphate salt until said urea is metabolized by bacteria in plaque.

2. A method employing a solution according to claim 1, wherein said fluroide salt is also a phosphate salt.

3. A method employing a solution according to claim 1, wherein said fluoride salt is $Na_2PO_3F$ present in a concentration such that the total fluoride concentration in the solution is about 5 mM.

4. A method employing a solution according to claim 1, wherein the pH is from about 4 to 5.

5. A method employing a solution according to claim 1 in the form of a mouth rinse which comprises an aqueous solution comprising 3% (W/V) urea, 20 mM calcium chloride, 12 mM sodium dihydrogen phosphate, 4.72 mM sodium monofluorophosphate, 0.28 mM sodium fluoride, 5% (V/V) glycerol, saccharine, spearmint and vanilla in amounts sufficient to increase palatability, and food color, said solution being adjusted to a pH of about 5.0.

6. A solution in the form of a mouth rinse which comprises an aqueous solution comprising 3% (V/V) urea, 20 mM calcium chloride, 12 mM sodium dihydrogen phosphate, 4.72 mM sodium monofluorophosphate, 0.28 mM sodium fluoride, 5% (v/v) glycerol, saccharine, spearmint and vanilla in amount sufficient to increase palatability, and food color, said solution being adjusted to a pH of about 5.0.

* * * * *